United States Patent [19]

Tamás et al.

[11] Patent Number: 4,748,023

[45] Date of Patent: May 31, 1988

[54] PROCESS FOR THE PREPARATION OF SUSTAINED RELEASE PHARMACEUTICAL COMPOSITIONS HAVING A HIGH ACTIVE INGREDIENT CONTENT

[75] Inventors: Éva Tamás, Gödöllő; Pál Fekete, Budapest; Tibor Kovács, Szentendre; Dénes Bezzegh, Budapest; Ilona Bór née Baumgartner, Budapest; Zoltán Tóth, Budapest; Katalin Zukovics née Sümeg, Budapest, all of Hungary

[73] Assignee: EGYT Gyógyszervegyészeti Gyár, Budapest, Hungary

[21] Appl. No.: 644,835

[22] PCT Filed: Jan. 25, 1984

[86] PCT No.: PCT/HU84/00006

§ 371 Date: Aug. 27, 1984

§ 102(e) Date: Aug. 27, 1984

[87] PCT Pub. No.: WO84/02843

PCT Pub. Date: Aug. 2, 1984

[30] Foreign Application Priority Data

Jan. 26, 1983 [HU] Hungary ............................. 245/83

[51] Int. Cl.$^4$ .................. A61K 9/50; A61K 9/52; A61K 9/22; A61K 9/26
[52] U.S. Cl. .................................... 424/465; 424/468; 424/469; 424/490; 424/494; 424/495; 424/497
[58] Field of Search ................ 424/19, 20, 22, 465, 424/468, 469, 490, 494, 495, 497

[56] References Cited

U.S. PATENT DOCUMENTS

| | | | |
|---|---|---|---|
| 2,853,420 | 9/1958 | Lowey | 424/37 |
| 2,996,431 | 8/1981 | Barry | 424/20 |
| 3,155,590 | 11/1964 | Miller et al. | 167/83 |
| 3,341,416 | 9/1967 | Anderson et al. | 167/83 |
| 3,488,418 | 1/1970 | Holliday et al. | 424/35 |
| 3,524,910 | 8/1970 | Holliday et al. | 424/35 |
| 3,557,279 | 1/1971 | Morse | 424/20 |
| 3,703,576 | 11/1972 | Kitajima et al. | 424/35 |
| 3,860,733 | 1/1975 | Morse et al. | 424/35 |
| 3,891,570 | 6/1975 | Fukushima et al. | 252/316 |
| 3,909,444 | 9/1975 | Anderson | 252/316 |
| 3,922,338 | 11/1975 | Estevenel et al. | 424/21 |
| 3,951,851 | 4/1976 | Kitajima et al. | 252/316 |
| 4,113,816 | 9/1978 | Estevenel | 264/113 |
| 4,415,547 | 11/1983 | Yu et al. | 424/20 |

FOREIGN PATENT DOCUMENTS

1380171  1/1975  United Kingdom ................ 424/465

OTHER PUBLICATIONS

Salib et al., Pharma 21E 31: 721–723 (1976).
Jalsenjak et al., J. Pharm. Pharmac., 28: 912–914 (1976).
Kornblum, J. Pharm. Sci., 62(1): 43–49, Jan. 1973: A New Tablet Disintegrating Agent.
Khan, Mfg. Chem., Jan. 1976, pp. 25–26, "Choosing the Right Tablet Disintegrant".
Khan, J. Pharm. Pharmac., 28: 633–636 (1976), Effect of Disintegrant Type Upon the Relationship Between Compressional Pressure and Dissolution Efficiency.
Gissinger, Drug Development and Industrial Pharmacy 6(5): 511–536 (1980).
Rudnic, Drug Development and Industrial Pharmacy 6(3): 291–309 (1980).
Van Kamp, Pharm. Week Bl. Sci. Ed. 5(4): 165–171 (1983).
Remington Pharm. Science, 15th Ed., pp. 1266, 1259, 1578, 1579, 1615.
Physicians Desk Reference, 31st Ed., 1977, pp. 1058, 1306, 777, 870.
Azhgikhin, I. S., "Technologia Gevarsta", 1975, Meditsina (Moscow), pp. 337–348, 350, 351.

*Primary Examiner*—Shep K. Rose
*Attorney, Agent, or Firm*—Schweitzer & Cornman

[57] ABSTRACT

The invention relates to a process for the preparation of sustained release solid pharmaceutical compositions having an active ingredient content of at least 80% and possessing a structure which loosens in aqueous medium but does not disintegrate to discrete particles within 4 hours which comprises coating the particles of the active ingredient in a liquid medium with a water insoluble polymer—preferably with an ethyl cellulose polymer film—and thereafter admixing the coated crystals with at least one disintegrating agent being capable of swelling in aqueous medium and other auxiliary agents conventionally used in pharmaceutical industry and pressing the mixture into tablets.

The advantage of the process of the present invention is that it is readily feasible with a very wide range of active ingredients and provides sustained release tablets having a high active ingredient content.

7 Claims, No Drawings

PROCESS FOR THE PREPARATION OF SUSTAINED RELEASE PHARMACEUTICAL COMPOSITIONS HAVING A HIGH ACTIVE INGREDIENT CONTENT

TECHNICAL FIELD

This invention relates to a process for the preparation of sustained release pharmaceutical compositions having a high active ingredient content.

BACKGROUND ART

The advantages of sustained release pharmaceutical compositions are well-known and their use is becoming more and more widespread. The methods used in this field of pharmaceutical industry are continuously developping. However the requirements raised against sustained release compositions are considerably higher and more severe than those raised against conventional pharmaceutical compositions. For this reason there is not yet known any process which can be applied for every active ingredient and meets all requirements. The preparation of sustained release pharmaceutical compositions from active ingredients having a relatively high therapeutical dose is particularly encountered with difficulties because the solid oral pharmaceutical compositions are of a limited size (the weight of a single dosage unit form can not be generally more than 0.8–1.0 g) and for this reason the known methods wherein the protracted effect was achieved with the aid of a relatively higher amount of auxiliary agents (the amount of the said auxiliary agent was approximately the same as that of the active ingredient) were applicable not at all or but to a very limited extent.

Sustained release pharmaceutical compositions corresponding to a relatively high single dosage unit of 100–500 mg can be prepared first of all in the form of matrix tablets. This is due to the fact that pharmaceutical compositions which have the lowest specific volume and may be hence most easily swallowed can be manufactured by pressing.

According to U.S. Pat. No. 2,895,881 waxes or fatty substances or hydrogenated castor oil can be used as release retarding agent in the preparation of matrix tablets. For this purpose glycerol monostearate (U.S. Pat. No. 2,993,839), a mixture of stearic acid and castor oil (U.S. Pat. No. 2,736,628), waxes, a mixture of waxes and water insoluble substances and mixture of waxes and hydrophylic polymers (U.S. Pat. Nos. 4,132,753, 3,402,240, 3,459,850 and 3,487,138) can also be applied. According to U.S. Pat. Nos. 2,987,445 and 3,317,394 water insoluble polymers, polyethylene and polymethyl-methacrylate and polivinyl chloride can be used as release retarding agent.

It is also known that a mixture of waxes and water insoluble polymers (U.S. Pat. No. 3,965,256), mixtures of polymers which readily swell in water and form mucus (U.S. Pat. No. 3,065,143), polymers forming complex with each other in water (carbopol; an acrylic acid polymerisate) and polyvinyl pyrrolidone (U.S. Pat. No. 3,458,622) and a mixture of carbopol and polyoxyethylene glycole (U.S. Pat. No. 3,634,584) can also be used as release retarding agent. In British Pat. No. 935,672 the use of protein derivatives while in U.S. Pat. No. 3,062,720 the use of water insoluble substances (e.g. talc, calcium sulfate, calcium hydrogen phosphate etc.) is reported. According to U.S. Pat. No. 3,905,508 a mixture of talc, ethyl cellulose and a metal stearate is used.

The matrix tablets disclosed in the said references comprise 10–70% of active ingredient. Sustained release tablets having a higher active ingredient content than the above value can only be prepared from active ingredients being poorly soluble in aqueous medium (to less than 1%).

According to the cited patent specifications matrix tablets are prepared by means of conventional granulating methods (by wet or dry granulation) or in the case of fatty substances by melting the said materials and encorporating the active ingredient into the liquid matrix material.

DISCLOSURE OF INVENTION

The object of the invention is to overcome the above drawbacks of the known methods and to provide a process for the preparation of sustained release pharmaceutical compositions which process is applicable to any active ingredient and ensures a high active ingredient content.

Thus the present invention relates to sustained release solid pharmaceutical compositions having a high active ingredient content—more than 80%—prepared by pressing a mixture of particles of the active ingredient coated with a film being insoluble in aqueous medium and at least one disintegrating agent capable of swelling in aqueous medium. The pharmaceutical compositions may also contain further auxiliary agents (e.g. filling materials, lubricants and sliding agents etc.). It is an essential feature of the present invention that the crystal particles of the active ingredient are coated in liquid phase by microencapsulation. The release of the active ingredient from the solid pharmaceutical composition is slowed down by the "barrier" effect of the water insoluble matrix structure formed during pressing from the film which coats the crystal particles. The substance being capable of swelling in water loosens the structure of the matrix and enables the penetration of the dissolving medium into the inner layers of the matrix. Thus the release of the active ingredient takes place within about 8 hours being optimal for oral absorption. The release velocity (rate) can be optionally changed by modifying the chemical composition and amount of the film forming agent and the disintegrating agent and can be adjusted to the value being optimal for therapeutical application.

It has been found that release rate can be appropriately decreased and release can be retarded also in the case of active ingredients readily soluble in water by applying first onto the crystal particles of the active ingredient a water insoluble coating by means of microencapsulation in liquid phase and thereafter passing tablets from the microcapsules thus obtained with at least one disintegrating agent capable of swelling in water, whereby the said disintegrating agent is used in such an amount which only loosens the structure of the tablet in aqueous medium but causes no disintegration to discrete particles.

The use of microencapsulation methods for the preparation of sustained release pharmaceutical compositions is known per se. However according to the hitherto known processes in most cases a relatively high amount of wall-material was required to retard the release of the active ingredient. According to U.S. Pat. No. 3,557,279 a triple amount of ethyl cellulose is used in the preparation of microcapsules containing indomethacine and having a suitable release velocity (rate). According to Pharmazie 10, 721-723 (1976) and J. of Pharmacy and Pharmacology 912-914 (1976) the release of chloramphenicol and sodium phenobarbital is retarded by preparing microcapsules in which the ratio of active ingredient and ethyl cellulose wall-material amounts to 1:2, 1:1 and 2:1, respectively. According to U.S. Pat. No. 3,909,444 the active ingredient is first granulated with a polymer being insoluble in acidic medium and thereafter the granules thus obtained having a matrix structure are coated with ethyl cellulose.

In order to protect the wall of the microcapsules from damages microcapsules are generally applied either filled into hard gelatine capsules or in suspension. When such microcapsules are pressed into tablets, special safety measures are to be taken to maintain the rate of release on the original value. According to U.S. Pat. No. 3,922,338 microcapsules diluted with a large—1 to 1,5 fold—amount of filling material are introduced into the middle layer of sandwich-structure tablets consisting of three layers. In the case of acetyl salicylic acid the use of crystals of suitable particle size (0.15-1.8 mm) and suitable form (the ratio of the size of the edges of crystal particles amounts to 1:2:4) protects the microcapsules from damages during pressing and provides a disintegrating time shorter than 1 minute (within an hour the release of the active ingredient is below 70%—U.S. Pat. specification Nos. 3,488,418 and 3,524,910). In this particular case the special and favourable properties of acetyl salicylic acid enable the preparation of pharmaceutical compositions exhibiting a protracted therapeutical effect for about 8 hours in spite of the relatively rapid (not longer than 4 hours) release.

Microencapsulation of acetyl salicylic acid is discussed in several U.S. Pat. specifications (e.g. U.S. Pat. Nos. 3,341,416, 3,155,590, 3,703,576, 3,951,851 and 3,891,570). According to the said citations the ratio of core-material and wall-material amounts to 1:50-1:1 but the said U.S. patent specifications are completely silent in disclosing any data about the changes of the microcapsules during pressing. In the said U.S. patent specifications the use of several polymers is mentioned—e.g. cellulose acetate, cellulose acetate phthalate, hydroxypropyl-methyl-cellulose-acetate-phthalate; various ethyl cellulose derivatives are most frequently used.

Thus it can be stated that with the only exception of acetyl salicyclic acid there is not known any process for the preparation of sustained release pharmaceutical compositions having an active ingredient content above 80% by microencapsulation.

On studying the release of the active ingredient from tablets pressed from microencapsulated active ingredients it has been found that when rapidly disintegrating tablets are prepared the release becomes rapid as a result of the damages of the wall of the microcapules caused during pressing. This release rate is substantially the same as that of conventional tablets, i.e. within an hour a 100% release is obtained. On the other hand if microcapsules are pressed to tablets per se or by adding only a lubricant, the release rate slows down to a great extent and a 100% release can be achieved but within 8-10 hours. In the latter case the release retarding is attributable to the cross-linked matrix structure formed from the wall of the microcapsules during pressing. It has been found in a surprising manner that the said cross-linked matrix-structure brings about a very significant release retarding effect already in a relatively small amount—preferably 2-18% by weight. The release rate can be controlled by modifying the amount of matrix material (i.e. that of the wall-material of the microcapsules) and the pressing strength. It has been found however that the release rate of the compositions can not be optionally modified just by varying the said two parameters. The release is either too rapid or so low that complete release of the active ingredient does not take place even within 8-10 hours.

It has been found that if to microcapsules—from which by pressing only tablets possessing too slow release properties can be prepared—a disintegrating agent capable of swelling in water is added in such an amount which does not cause disintegration of the tablets to discrete particles having a particle size smaller than 1 mm but merely loosens in aqueous medium the structure of matrix, the release of the active ingredient can be modified within very broad limits in a highly reproducible manner. For this purpose any suitable disintegrating agent generally used in the manufacture of tablets can be applied, e.g. starch and derivatives thereof, carboxy methyl starch, carboxymethyl cellulose, formaldehyde caseine, cross-linked polyvinyl pyrrolidone etc.

Practically any film-forming polymer material being insoluble in aqueous medium can be used for the preparation of microcapsules, e.g. cellulose acetate, polyvinyl acetate, polivinyl butiral, particularly ethyl cellulose. Microencapsulation can be carried out with the aid of any suitable microencapsulating process known per se which is capable of forming an uniform continuous coating on the surface of the crystal particles of the active ingredient. In the case of ethyl cellulose a process carried out in cyclohexane as medium and disclosed in U.S. Pat. No. 3,531,418 and British Pat. No. 2,002,318 can be preferably applied. If other polymers are used one may carry out the solvent evaporating methods described in U.S. Pat. specifications Nos. 3,891,570 and 3,951,851.

The particle size of the active ingredient used for microencapsulation plays no decisive role and may be any optional value. In order to form a continuous coating on the surface of the particles it is preferred to grind crystalline substances to a particle size below 50 $\mu$m. The quality of the coating can be checked in a simple manner by means of a polarization microscope.

The in vitro release of crystalline particles (microcapsules) coated with a uniform layer is studied by microscopic measurements. It has been found that even if the amount of the coating substance is 10-18% the release rate is too large—about 90-100% within an hour—this means that the microcapsules are suitable for the preparation of sustained release pharmaceutical compositions neither per se nor if filled into hard gelatine capsuls. It is therefore indispensable to convert the microcapsules to matrix tablets by pressing.

According to the present invention there is provided a process for the preparation of sustained release solid pharmaceutical compositions having an active ingredient content of at least 80% and possessing a structure which loosens in aqueous medium but does not disintegrate to discrete particles within 4 hours which comprises coating the particles of the active ingredient in a liquid medium with a water insoluble polymer—preferably with an ethyl cellulose polymer film—and thereafter admixing the coated crystals with at least one disintegrating agent being capable of swelling in aqueous medium and other auxiliary agents conventionally used in pharmaceutical industry and pressing the mixture into tablets.

According to the process of the present invention sustained release tablets comprising at least 80% of the active ingredient can be prepared. In the first step of the process of the present invention the particles of the active ingredient are subjected to microencapsulation. This may be particularly advantageously carried out by microencapsulation with ethyl cellulose in cyclohexane as medium. The crystal particles of the active ingredient and 2–18% of ethyl cellulose—related to the active ingredient—(preferably a product designated as N-100 manufactured by the firm Hercules) are dispersed in so much cyclohexane that the ethyl cellulose concentration should amount to 2–5%. The system is warmed to 80° C., kept at this temperature for an hour and cooled slowly to room temperature. In order to improve the uniform character of the coating of the microcapsule in some cases polyisobutylene may be added to the system or the particles of the active ingredient are ground to a particle size below 50 μm. From the cooled system the microcapsules are filtered off, dried, sieved, admixed with a suitable disintegrating agent and optionally with lubricants and finally pressed into tablets of high solidity.

In the case of certain active ingredients the parameters which ensure optimal release rate (e.g. starting particle size of the active ingredient, amount of ethyl cellulose, character and amount of the disintegrating agent etc.) can not be given in advance but are to be determined by experiments which belong to the obligatory knowledge of the skilled art worker and can be easily performed.

INDUSTRIAL APPLICABILITY

The process of the present invention can be widespreadly used in pharmaceutical industry for the preparation of sustained release tablets. The advantage of the process of the present invention is that it is generally applicable for a wide range of active ingredients and provides sustained release tablets having a high active ingredient content about 80%.

Modes of Carrying out the Invention

Further details of the present invention are to be found in the following Examples without limiting the scope of protection to the said Examples.

EXAMPLE 1

Preparation of sustained release tablets comprising L-α-methyl-dopa (L-α-methyl-3.4-dihydroxy-phenylalanine) as active ingredient Into a 2 l round-bottomed flask equipped with a reflux condenser and a stirrer 200 g of L-α-metyl-dopa (particle size below 50 μm) and 20 g of ethyl cellulose (quality: N-100, ethoxy content: 47.5–49%, viscosity 100 mPa measured at 25 C.° in a 5% by weight 80:20 toluene—ethanol mixture) and 1000 ml of cyclohexane are introduced.

The powder is suspended under constant rate of stirring—about 200-250 r.p.m.—and the system is warmed to 80 C.° with the aid of a water bath. The mixture is refluxed under stirring at this temperature for 30 minutes and allowed to cool to 40 C.° within about an hour under constant stirring. On cooling the particles become coated with ethyl cellulose. The system is cooled with cold water below 20 C.°, the microcapsules are isolated by filtration and dried at room temperature on a tray. On sieving the product thus obtained on a 1 mm sieve, free-flowable non-sticking and non-adhering granules are obtained. Under microscope the product consists predominantly of almost isodiametrical agglomerates of 100–300 μm which do not show any crystalline character in polarized light. If L-α-methyl-dopa having a particle size larger than 100 μm is used for microencapsulation, the peaks of the crystal particles are not coated by ethyl cellulose.

In a double-conical mixing apparatus the following powder mixtures are prepared from the above microcapsules by homogenizing for 20 minutes.

| Component | Amount in the mixture (g) | | | |
|---|---|---|---|---|
| | I. | II. | III. | IV. |
| L-α-methyl-dopa microcapsules | 88.7 | 88.7 | 88.7 | 88.7 |
| Microcrystalline cellulose | 10.3 | 6.3 | 6.3 | 9.4 |
| Potato starch | — | — | 4.0 | — |
| Sodium carboxy methyl cellulose (Nymcel) | — | 4.0 | — | 0.9 |
| Magnesium-stearate | 1.0 | 1.0 | 1.0 | 1.0 |
| | 100.0 | 100.0 | 100.0 | 100.0 |

The powder mixture thus contained is pressed into tablets comprising 500 mg of L-α-methyl-dopa, having a diameter of 12 mm and a breaking strength of 100–120 kN.

The release of the active ingredient is determined by the "half-change" method under using a disintegration testing apparatus according to USP XX. Dissolving is started in the first hour with artificial gastric fluid and the half of the dissolving medium is replaced in each hour by artificial intestinal fluid.

The composition of artificial gastric fluid is as follows:

| | |
|---|---|
| Sodium chloride | 2 g |
| N hydrochloric acid | 80 ml |
| Filled up with distilled water to | 1000 ml |

The composition of the artificial intestinal fluid is as follows:

| | |
|---|---|
| Disodium hydrogen phosphate | 8.05 g |
| Sodium dihydrogen phosphate | 1.56 g |
| Filled up with distilled water to | 1000 ml |

During the test 6 tablets are placed into each container of the apparatus and the said containers are moved in a beaker thermostated at 37 C.° and comprising 800 ml of dissolving medium vertically with an amplitude of 2.5 cm and a speed of 30 cm/sec. After the half of the dissolving medium has been replaced, the L-α-methyl-dopa concentration of the residual liquid is spectro-photometrically determined.

The results of the release experiment are summarized in the following Table:

| Release time (in hours) | Amount of released active ingredient, % | | | |
|---|---|---|---|---|
| | I. | II. | III. | IV. |
| 1 | 26.5 | 98.3 | 44.5 | 44.0 |
| 2 | — | — | 55.8 | 55.9 |

| Release time | Amount of released active ingredient, % | | | |
|---|---|---|---|---|
| (in hours) | I. | II. | III. | IV. |
| 3 |  |  | 66.8 | 71.1 |
| 4 | 36.6 | — | 75.7 | 92.9 |
| 5 | 39.6 | — | 82.9 | 92.9 |
| 6 | 42.8 | — | 89.0 | 99.4 |
| 7 | 46.4 | — | — | 102.2 |
| 8 | 50.0 | — | — | — |

On the basis of the above in vitro release tests compositions III and IV of the present invention meet the requirements of sustained release compositions. The release of composition I containing no disintegrating agent is too slow while that of composition II containing a large amount of Nymcel is too rapid because the tablet disintegrates within 5 minutes. On decreasing the amount of Nymcel the desired release rate can be adjusted.

EXAMPLE 2

Preparation of sustained release Trimethoprim tablets

In this Example the effect of the ethyl cellulose content and disintegrating agent content of the microcapsules and that of the size of pressing strengh on the release of active ingredient is demonstrated.

Into the apparatus according to Example 1 1000 ml cyclohexane are introduced, 10 g of polyisobutylene (Oppanol, molecular weight 90,000) are dissolved and to the solution thus obtained 200 g of trimethoprim [2.4-diamino-5-(3′, 4′,5′-trimethoxy-benzyl)-pyrimidine; particle size below 200 μm] and in three batches ethyl cellulose in three different amounts [10 g, 20 g and 30 g, respectively; quality as described in Example 1] are added. The system is stirred at a rate of 200 r.p.m. and worked up according to Example 1.

The microcapsules are homogenized with potato starch and magnesium stearate; the amount of the said components is disclosed in the following Table. The mixture is pressed on an eccentric tablet-manufacturing machine equipped with a dynamometer comprising a strain gauge into tablets containing 200 mg of trimethoprim and having a diameter of 10 mm.

Release tests are carried out in the apparatus described in Example 1 except that the artificial gastric fluid of the given composition is used throughout the whole experiment and samples of 10 ml are taken in every hour for spectrophotometrical analysis.

The composition of the powder mixture, the pressing strength and the release of the active ingredient from the tablets are disclosed in the following Table.

| Ratio of ethyl cellulose and trimethoprim | 1:20 | | | | 1.5:20 | | | | 2:20 | | | |
|---|---|---|---|---|---|---|---|---|---|---|---|---|
| Pressing strength (kN) | 10000 | | 15000 | | 10000 | | 15000 | | 10000 | | 15000 | |
| No. of powder mixture | 1 | 2 | 3 | 4 | 5 | 6 | 7 | 8 | 9 | 10 | 11 | 12 |
| Trimethoprim microcapsule (g) | 98 | 94 | 98 | 94 | 94 | 92 | 94 | 92 | 94 | 92 | 94 | 92 |
| Potato starch (g) | 1 | 5 | 1 | 5 | 5 | 7 | 5 | 7 | 5 | 7 | 5 | 7 |
| Magnesium stearate (g) | 1 | 1 | 1 | 1 | 1 | 1 | 1 | 1 | 1 | 1 | 1 | 1 |
| Release time (hours) | Released trimethoprim, % | | | | | | | | | | | |
| 1 | 58 | 76 | 45 | 55 | 21 | 41 | 15 | 32 | 20 | 31 | 17 | 22 |
| 2 | 68 | 87 | 64 | 68 | 31 | 53 | 21 | 33 | 24 | 43 | 23 | 30 |
| 3 | 77 | 91 | 68 | 74 | 35 | 65 | 22 | 39 | 26 | 47 | 29 | 34 |
| 4 | 89 | 95 | 75 | 81 | 41 | 71 | 29 | 45 | 30 | 59 | 30 | 40 |
| 5 | 91 | 97 | 81 | 87 | 48 | 80 | 36 | 50 | 38 | 69 | 37 | 45 |
| 6 | — | — | — | — | 66 | 82 | 38 | 57 | 46 | 73 | 40 | 52 |
| 7 | — | — | — | — | 73 | 84 | 44 | 63 | 54 | 76 | 46 | 59 |

It appears from the above Table that the release of tablets prepared from microcapsules in which the ratio of ethyl cellulose to trimethoprim amounts to 1:20 is too rapid already in the presence of 1% of potato starch, while in the case of microcapsules which correspond to an ethyl cellulose to trimethoprim ratio of 2:20 more than 7% of potato starch are required to ensure complete release rate.

The above experimental results clearly show the effect of certain parameters on the release rate and the optimal composition can be determined by taking into consideration the said effects.

EXAMPLE 3

Preparation of sustained release potassium chloride tablets

Potassium chloride is microencapsulated according to Example 1 by using 200 g of potassium chloride (particle size below 71 μm) and 20 g of ethyl cellulose (N100).

From the microcapsules a powder mixture having the following composition is prepared:

| Potassium chloride microcapsule | 98.0 g |
|---|---|
| Potato starch | 1.0 g |
| Magnesium stearate | 1.0 g |

From the homogenisate tablets having a diameter of 12 mm, a potassium chloride content of 500 mg and a breaking strength of 100–120N are prepared. The potassium chloride release of the said tablets is shown in the following Table:

| Release time (hours) | Released potassium chloride % |
|---|---|
| 1 | 29 |
| 2 | 41 |
| 3 | 48.5 |
| 4 | 53 |
| 5 | 62 |
| 6 | 67 |
| 7 | 73 |

The release rate is determined in an Erweka type disintegration testing apparatus according to USP XX by using distilled water as dissolving medium and determining the amount of released potassium chloride by measuring conductivity.

EXAMPLE 4

Preparation of sustained release teophylline tablets

Microencapsulation is carried out according to Example 2 by using 200 g of teophylline (particle size below 500 μm) as core-material and 20 g of ethyl cellulose (type N 100) as coating material.

From the said microcapsules a powder mixture having the following composition is prepared:

| | |
|---|---|
| Teophylline microcapsules | 275.0 g |
| Microcrystalline cellulose | 5.5 g |
| Lactose (monohydrate) | 18.0 g |
| Magnesium stearate | 1.5 g |
| Total weight | 300.0 g |

From the powder mixture tablets having a diameter of 10 mm, a breaking strength of 80N, weighing 300 mg and comprising 250 mg of teophylline as active ingredient are pressed. The release rate as determined according to Example 2 and the following results are obtained:

| Release time (hours) | Released teophylline % |
|---|---|
| 1 | 19.1 |
| 2 | 29.5 |
| 3 | 39.0 |
| 4 | 52.9 |
| 5 | 68.4 |
| 6 | 82.7 |

What we claim is:

1. A compressed relatively large single sustained release and dosage unit tablet which consists essentially of:
   (a) at least 80% by weight of 100 to 500 mg. of at least one pharmacologically active ingredient, encapsulated in
   (b) an effective amount of a pharmaceutically acceptable water insoluble polymer for microencapsulating said active ingredient and for retarding the dissolution of the active ingredient within the human body for a predetermined period of time, said effective amount being from about 2% to about 18% by weight of said tablet, and admixed therewith
   (c) an effective amount of from about 0.9% to about 25% by weight of the tablet of a pharmaceutically acceptable, water swellable disintegrating agent for loosening the structure of the compressed tablet in water or like body fluid without disintegration of the tablet into discrete particles for a period of at least 4 hours, said tablet having been compressed at a predetermined force effective cooperatively with said polymer and said disintegrating agent to form a cross-linked matrix structure from the walls of the microcapsules during pressing a matrix structure which loosens upon aqueous swelling, to regulate the release at a predetermined rate of said active ingredient from said tablet.

2. The tablet of claim 1, wherein said disintegrant comprises from about 0.9 to about 25% by weight of the tablet.

3. The tablet of claim 1, wherein said polymer is a cellulosic, butyral, butylene, or vinyl polymer.

4. The tablet of claim 3, wherein said polymer is ethyl cellulose, cellulose acetate, vinyl butyral, isobutylene, or vinyl acetate polymer.

5. The tablet of claim 1, wherein said disintegrant is at least one of microcrystalline cellulose, potato starch, carboxymethyl starch, formaldehyde casein, cross-linked polyvinylpyrrolidone, magnesium stearate, and lactose.

6. The tablet of claim 1, wherein the active ingredient is L-alpha methyl dopa, trimethoprim, theophylline, potassium chloride, or a pharmaceutically acceptable salt thereof.

7. The tablet of claim 5, wherein said disintegrant comprises from about 0.9 to about 25% by weight of the tablet, said polymer is an ethyl cellulose, cellulose acetate, vinyl butyral, isobutylene, or vinyl acetate polymer, and the active ingredient is L-alpha methyl dopa, trimethoprim, theophyilline, or potassium chloride, or a phamaceutically acceptable salt thereof.

* * * * *